United States Patent [19]

Horikawa et al.

[11] Patent Number: 5,959,141
[45] Date of Patent: Sep. 28, 1999

[54] 1-AMINO-2-HYDROXYCYCLOALKANECARBOXYLIC ACID DERIVATIVES

[75] Inventors: Manabu Horikawa, Ibaraki; Yasufumi Ohfune, Takatsuki, both of Japan

[73] Assignee: Suntory Limited, Osaka, Japan

[21] Appl. No.: 09/037,906

[22] Filed: Mar. 10, 1998

[30] Foreign Application Priority Data

Sep. 9, 1997 [JP] Japan .................................. 9-259439

[51] Int. Cl.$^6$ .......................... C07C 61/06; C07C 61/04; C07C 61/08
[52] U.S. Cl. .......................... 562/504; 562/505; 562/507
[58] Field of Search .................................. 562/504, 505, 562/507

[56] References Cited

PUBLICATIONS

Database CAPLUS on STN, Acc. No. 1997:564947, Christensen et al., 'Does the non-saturable cell entry apply to the charge-free form of amiono acids?,' abstract, 1977.

D.E. Gaitanopoulos et al., Racemic Diastereoisomers of 1-Amino-2-Hydroxycyclopentanecarboxylic Acid *J. Med. Chem* 19(2):342-344 (1976).

M. Horikawa et al., "Asymmetric Syntheses of Both Enantiomers of α-Benzylserine and β-Carboxymethylserine" *Synlett* 253-254 (1997).

Y. Ito et al., "Asymmetric Aldol Reaction of α-Isocyanocarboxylates with Paraformaldehyde Catalyzed by Chiral Ferrocenylphosphine-Gold (I) Complexes" *Tetrahedron Letters* 29(2):235-238 (1988).

S.-H. Moon et al., "Efficeint Syntheses of the Four Enantiomers and Diastereomers of α-Methylthreonine and Both Enantiomers of α-Methylserine" *J. Am. Chem. Soc.* 116(16):7405-7406 (1994).

D. Seebach et al., "α-Alkylation of Threonine" *Tetrahedron Letters* 24(32):3311-3314 (1983).

Abstract of the presentation at the 72nd Spring Annual Meeting of the Chemistry Society of Japan on Mar. 27, 1997 entitled, "Synthesis and Bioactivity of α, α-Disubstituted-β-Amino Acid-Introduced Peptides," and an English language translation thereof, along with a set of overhead drawings presented at the meeting.

Abstract of the presentation at the 71st Symposium on Organic Synthesis, Japan on Jun. 5, 1997 entitled, "Synthesis of Compounds for Bioactivity," and an English translation thereof, along with a set of overhead drawings presented at the symposium.

*Primary Examiner*—Gary Geist
*Assistant Examiner*—Brian J. Davis
*Attorney, Agent, or Firm*—Testa, Hurwitz & Thibeault, LLP

[57] ABSTRACT

The invention is directed to optically active 1-amino-hydroxycycloalkanecarboxylic acid compounds represented by the formula:

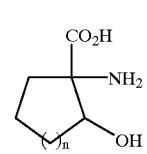

(I)

wherein n is 0, 1, 2, 3, or 4; methods of their synthesis; and their use as compounds to fix the confirmation of a peptide or protein molecule when introduced into the peptide or protein in the place of a normal amino acid.

16 Claims, 2 Drawing Sheets

1-AMINO-2-HYDROXYCYCLOALKANECARBOXYLIC ACID DERIVATIVES

BACKGROUND OF THE INVENTION

1. Field of the Invention

The present invention relates to 1-amino-2-hydroxycycloalkanecarboxylic acid derivatives. More particularly, the invention relates to 1-amino-2-hydroxycycloalkanecarboxylic acid derivatives derived from α,α-disubstituted α-amino acids and optically active forms thereof.

The 1-amino-2-hydroxycycloalkanecarboxylic acid derivatives of the invention are those in which a hydroxyl group is introduced to the β-position of the carboxylic acid and the α- and the β-positions are linked to form a cyclic system whereby the conformation of the hydroxyl group at the β-position is controlled. When the 1-amino-2-hydroxycycloalkanecarboxylic acid derivative of the present invention is introduced into a peptide or protein molecule in place of a normal amino acid, the conformation of the obtained peptide or protein molecule can be fixed. Therefore, the compounds of the invention can play an important role in peptide and protein engineering.

The 1-amino-2-hydroxycycloalkanecarboxylic acid derivatives of the present invention can be regarded as cyclic amino acid derivatives equivalent to naturally occurring hydroxyamino acids such as serine and threonine.

2. Description of the Prior Art

Peptides having α-substituted amino acid(s) in the molecule have been arousing interest in their physiological activities because of their resistance against peptidases resulting from the steric hindrance at the peptide linkage sites and because of their enzyme-inhibiting activities resulting from the stabilized conformation in α-helical structure. For example, in peptides, when amino acids such as serine, phenylalanine and aspartic acid are replaced by α-substituted amino acids, hydrolysis of the peptide bonds with peptidases can be inhibited and the conformation of the peptides can be stabilized, and therefore such peptides have been drawing attention from a viewpoint of development of enzyme inhibitors and the like.

On the other hand, serine and threonine which constitute physiologically active peptide often act as the active centers of receptors and enzymes. Therefore, it has also been arousing interest to introduce an amino acid derivative having a conformationally controlled hydroxyl group into a peptide or protein molecule in place of naturally occurring amino acids such as serine and threonine and to study the effectiveness of such introduction on physiological activity and the correlation between the structure and the activity of the peptide or protein molecule.

Heretofore, several types of α-substituted amino acids have been reported, including α-substituted serine derivatives such as 2-methylserine (2-hydroxymethylalanine) and 2-phenylserine (2-hydroxymethyl-2-phenylglycine) (D. Seebach et al., Tetrahedron Letters., vol. 24, p.3311, 1983; Ito et al., ibid., vol.29, p.235, 1988), 2-hydroxymethylphenylalanine and 2-hydroxymethylaspartic acid (Japanese Patent Application Laid-open No. 8-337558).

However, any type of 1-amino-2-hydroxycycloalkanecarboxylic acid derivatives in which the conformation of the hydroxyl group at the β-position is controlled by cyclically linking the α-position and the β-position have not been reported yet, other than 5-membered cyclic racemic amino acids (D. E. Gaitanopoulous et al.,: J. Med. Chem., vol. 19, p.342, 1976).

SUMMARY OF THE INVENTION

In accordance with the present invention, there are provided 1-amino-2-hydroxycycloalkanecarboxylic acid derivatives which can be regarded as derivatives equivalent to β-hydroxyamino acids such as serine and threonine.

The 1-amino-2-hydroxycycloalkanecarboxylic acid derivatives of the present invention have asymmetric carbon atoms at the 1- and 2-positions therein and, therefore, have two kinds of stereoisomers, i.e., (1R, 2S) and (1R, 2R) configurations. Each of these stereoisomers has its enantiomer, i.e., (1S, 2R) and (1S, 2S) configurations, respectively.

Therefore, the present invention provides the 1-amino-2-hydroxycycloalkanecarboxylic acid derivatives as racemic mixtures, as well as isomers thereof in a stereoselective manner.

Accordingly, an object of the present invention is to provide a 1-amino-2-hydroxycycloalkanecarboxylic acid derivative represented by formula (I):

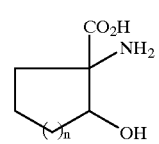

(I)

wherein n is 0, 1, 2, 3 or 4,
and an optically active form thereof.

In particular, the present invention provides two kinds of optically active forms of the compound of formula (I), namely (1R, 2S)-1-amino-2-hydroxycycloalkanecarboxylic acid represented by formula (1):

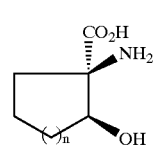

(1)

wherein n is 0, 1, 2, 3 or 4; and
(1R, 2R)-1-amino-2-hydroxycycloalkanecarboxylic acid represented by formula (2):

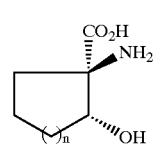

(2)

wherein n is 0, 1, 2, 3 or 4.

Another object of the present invention is to provide the 1-amino-2-hydroxycycloalkane carboxylic acids of formulae (1) and (2) in a stereoselective manner.

Accordingly, a more specific object of the present invention is to provide optically active 1-amino-2-hydroxycycloalkanecarboxylic acids having various numbers of carbon atoms in the cycloalkane ring (i.e., the n in formula (I) within the above-defined numbers) as listed below:

(1R,2S)-1-amino-2-hydroxycyclobutanecarboxylic acid;
(1R,2R)-1-amino-2-hydroxycyclobutanecarboxylic acid;
(1R,2S)-1-amino-2-hydroxycyclopentanecarboxylic acid;
(1R,2R)-1-amino-2-hydroxycyclopentanecarboxylic acid;
(1R,2S)-1-amino-2-hydroxycyclohexanecarboxylic acid;
(1R,2R)-1-amino-2-hydroxycyclohexanecarboxylic acid;
(1R,2S)-1-amino-2-hydroxycycloheptanecarboxylic acid;
(1R,2R)-1-amino-2-hydroxycycloheptanecarboxylic acid;
(1R,2S)-1-amino-2-hydroxycyclooctanecarboxylic acid;
(1R,2R)-1-amino-2-hydroxycyclooctanecarboxylic acid;
and enantiomers of (1S,2R) and (1S,2S) configurations thereof.

DETAILED DESCRIPTION OF THE INVENTION

Figure 1:
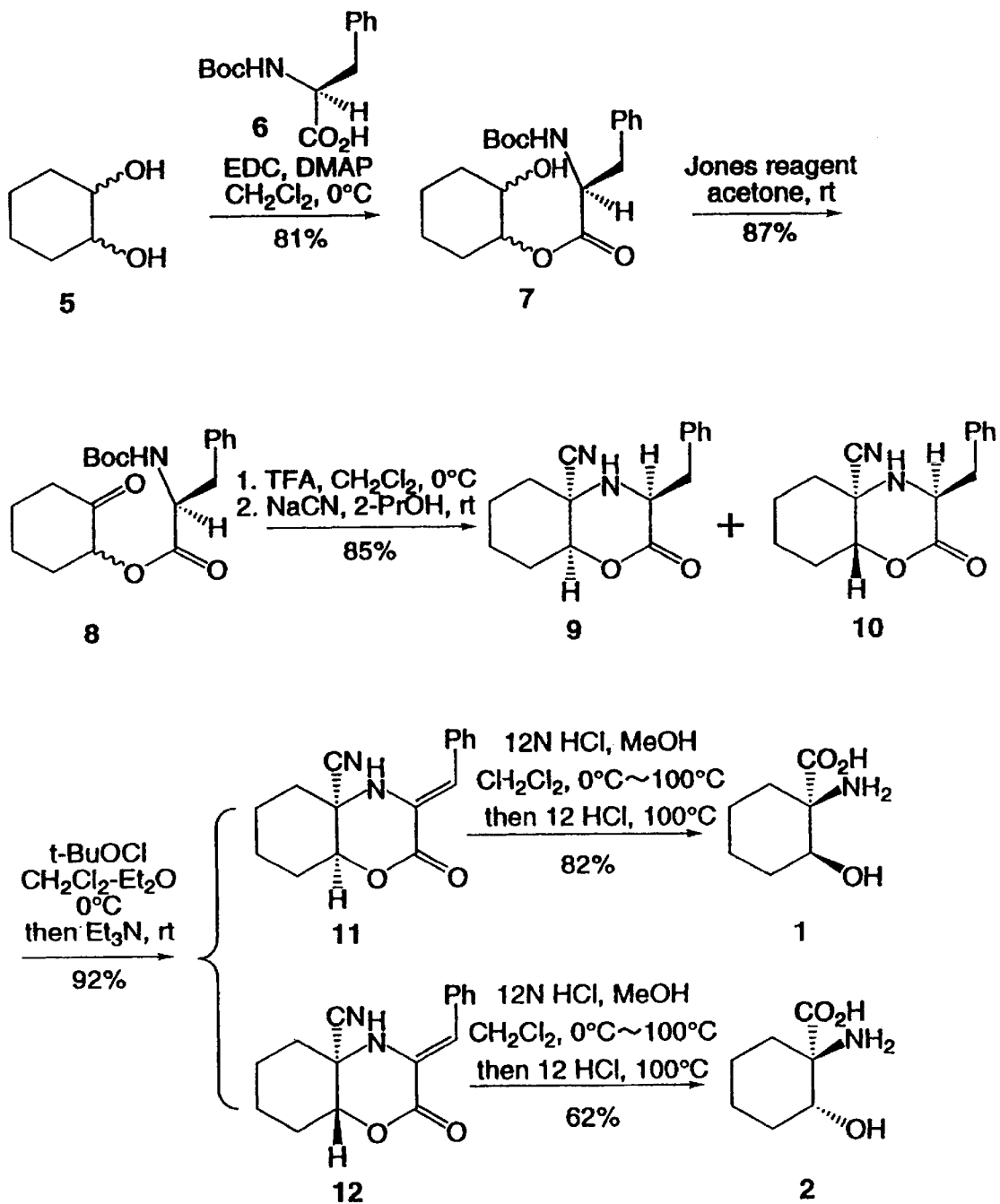
FIG. 1 is a schematic illustration of the process for synthesis of a compound of the invention.

The process for preparation of the optically active 1-amino-2-hydroxycycloalkanecarboxylic acids of the invention will be described below.

First, the process for synthesis of (1R,2S)-1-amino-2-hydroxycyclohexanecarboxylic acid represented by formula (1) (wherein n=2), which is a typical compound of those provided by the invention, is now explained. For the synthesis of this compound, 1,2-cyclohexanediol of formula (5), for example, is used as a starting compound.

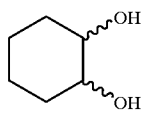

(5)

The 1,2-cyclohexanediol is condensed with N-t-butoxycarbonyl-L-phenylalanine of formula (6):

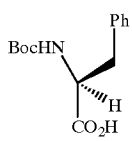

(6)

wherein "Boc" represents a t-butoxycarbonyl group, to give an ester of L-phenylalanine of formula (7):

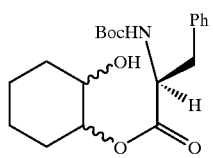

(7)

wherein "Boc" is as defined above.

The obtained ester is then treated with Jones reagent or the like to oxidize its secondary hydroxyl group, thereby giving a ketone of formula (8):

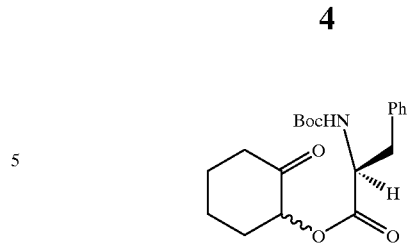

(8)

wherein "Boc" is as defined above.

The obtained ketone of formula (8) is treated with an acid such as trifluoroacetic acid (TFA) and hydrochloric acid to remove the t-butoxycarbonyl group therefrom and then subjected to cyclo-dehydration reaction with a cyanide (e.g., sodium cyanide, potassium cyanide, etc.) in an anhydrous lower alcohol (e.g., anhydrous methanol, anhydrous ethanol, anhydrous isopropanol, etc.) or anhydrous N,N-dimethylformamide, preferably in anhydrous isopropanol, thereby giving a mixture of (3S,4aS,8aS)-1,4-oxadine derivative of formula (9) and (3S,4aS,8aR)-1,4-oxadine derivative of formula (10).

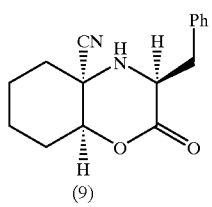 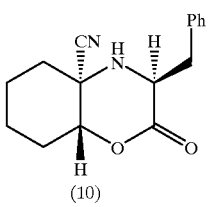

(9) (10)

At the time point where the cyclization reaction is completed, these compounds (9) and (10) can be isolated from each other, for example, by column chromatography. Alternatively, the mixture of compounds (9) and (10) per se may be treated with an oxidizing agent such as t-butylhypochlorite and then further treated with triethylamine to give a mixture of (4aS,8aS)-enamine derivative of formula (11) and (4aS,8aR)-enamine derivative of formula (12).

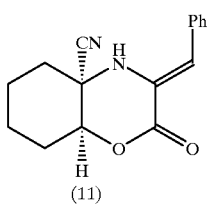 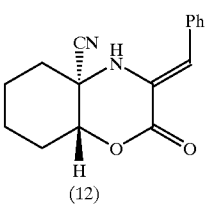

(11) (12)

After the completion of the reaction, the obtained mixture is subjected to isolation means such as column chromatography to isolate and purify compounds (11) and (12) from each other easily.

Alternatively, subjecting compound (9), which was isolated and purified after the completion of the above-mentioned cyclization reaction, to treatment with an oxidizing agent such as t-butylhypochlorite and then with triethylamine gives compound (11) as a single compound.

Compound (11) thus isolated and purified is treated with concentrated hydrochloric acid in an appropriated organic solvent which does not participate in the reaction (e.g., dichloromethane, methanol, etc.). Then, the solvent is removed and the residue is heated together with concentrated hydrochloric acid, thereby giving (1R,2S)-1-amino-2-hydroxycyclohexanecarboxylic acid represented by formula (1) (wherein n=2), which is one of the objective compounds of the invention.

On the other hand, compound (12), which can be obtained by isolation and purification after the completion of the conversion to the enamine derivatives, may be subjected to the same reaction procedure as above to give (1R,2R)-1-amino-2-hydroxycyclohexanecarboxylic acid represented by formula (2) (wherein n=2), which is also one of the objective compounds of the invention.

Another compound provided by the invention, (1R,2S)-1-amino-2-hydroxycyclopentanecarboxylic acid represented by formula (1) (wherein n=1), can be synthesized in the following manner:

2-Hydroxycyclopentanone dimethylacetal of formula (13):

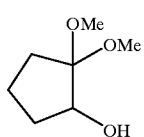

(13)

is condensed with N-t-butoxycarbonyl-L-phenylalanine of formula (6) to give an ester of L-phenylalanine of formula (14):

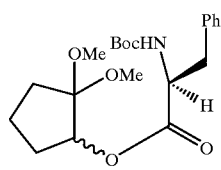

(14)

wherein "Boc" is as defined above.

Thereafter, the obtained ester (14) is treated with an acid to hydrolyze the dimethylacetal moiety, thereby giving a ketone of formula (15):

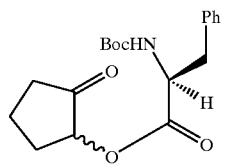

(15)

wherein "Boc" is as defined above.

The obtained ketone (15) is treated with an acid such as trifluoroacetic acid (TFA) and hydrochloric acid to remove the t-butoxycarbonyl group, thereby giving a TFA salt or hydrochloride of the ketone (15). The obtained TFA salt or hydrochloride is treated with anhydrous magnesium sulfate and sodium acetate in acetonitrile and then reacted with trimethylsilyl cyanide (TMSCN) and zinc chloride (ZnCl$_2$), thereby giving (3S,4aS,7aS)-1,4-oxadine derivative of formula (16) almost as a single product.

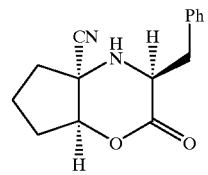

(16)

The obtained compound (16) is then treated with an oxidizing agent such as t-butylhypochlorite and then further treated with triethylamine to give a (4aS,7aS)-enamine derivative of formula (17):

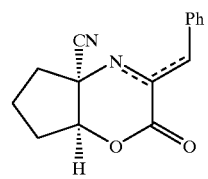

(17)

wherein dotted bonds indicate the presence/absence of a double bond at either site.

The enamine derivative (17) thus obtained is heated together with concentrated hydrochloric acid to give the objective compound, i.e., (1R,2S)-1-amino-2-hydroxycyclopentanecarboxylic acid represented by formula (1) (wherein n=1).

Figure 2:
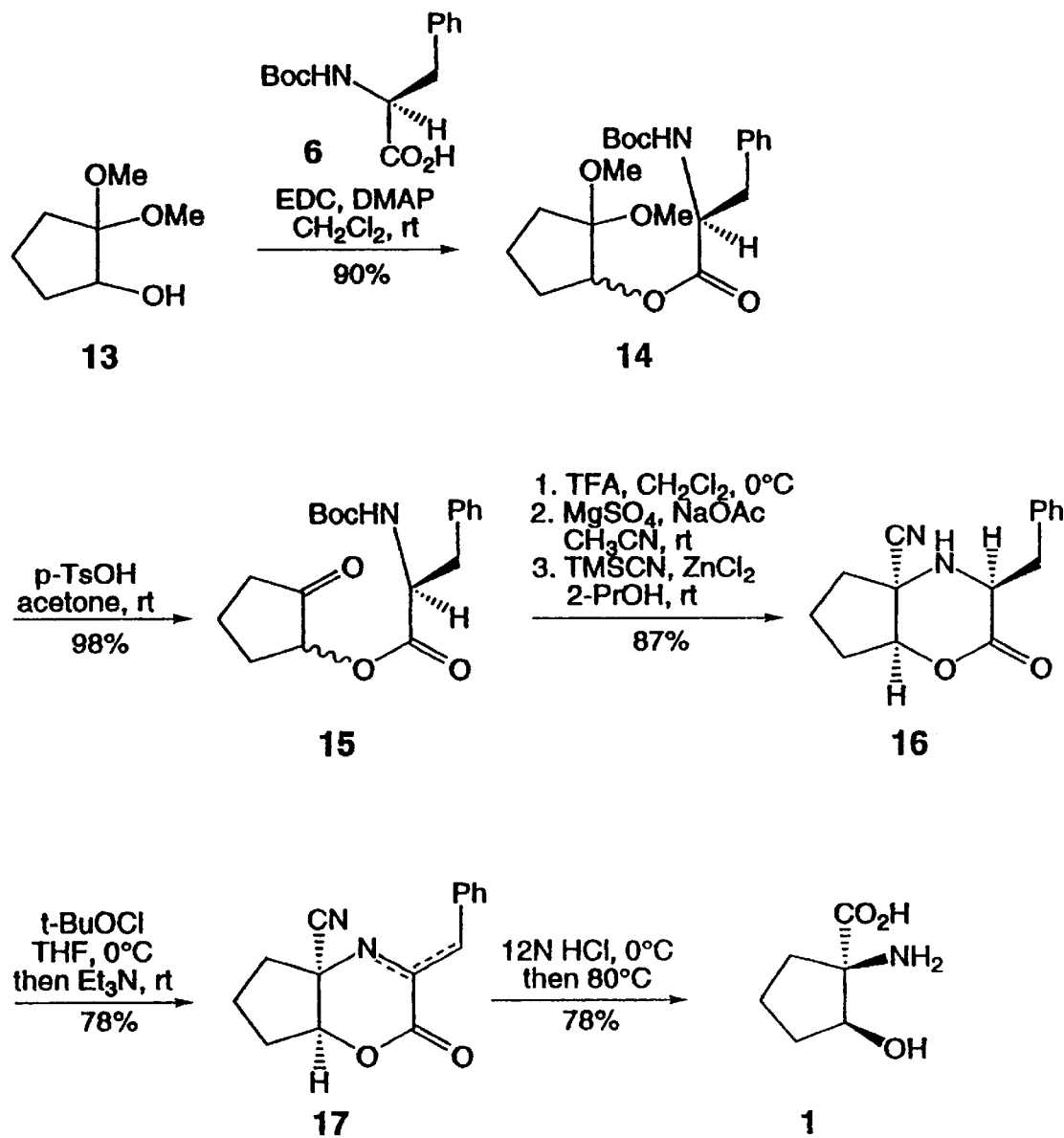
FIG. 2 is a schematic illustration of the process for synthesis of another compound of the invention.

The synthesis steps mentioned above are summarized in FIGS. 1 and 2.

Basically following the processes explained above, instead of the L-amino acid derivative of formula (6), the use of the corresponding D-amino acid as a starting compound enables to synthesize optically active 2-hydroxy-cyclic-amino acid derivatives of formulae (3) and (4):

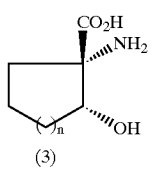 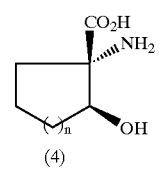

(3)  (4)

wherein n is 0, 1, 2, 3 or 4,
which are optical isomers of each other.

In addition, suitable selection of the diol compound, i.e., another starting compound, from 1,2-cyclobutanediol, 1,2-cycloheptanediol, etc. enables to synthesize other optically active 2-hydroxy-cyclic-amino acid derivatives of the invention having different numbers of ring-constituting carbons (e.g., n=0, 3, or 4.).

The present invention is described in more detail by way of the following examples; however, the present invention is not limited to those examples.

Example 1

(1R,2S)-1-Amino-2-hydroxycyclohexanecarboxylic acid (compound 1, n=2), and (1R,2R)-1-amino-2-hydroxycyclohexanecarboxylic acid (compound 2, n=2)

Step 1: Synthesis of N-t-butoxycarbonyl-L-phenylalanine 2-hydroxycyclohexyl ester (compound 7)

4.21 g (15.9 mmol) of N-t-butoxycarbonyl-L-phenylalanine, 1.94 g (16.7 mmol) of 1,2-cyclohexanediol and 4.56 g (23.8 mmol) of 1-ethyl-3-(3-dimethylaminopropyl)carbodiimide. HCl (EDC) were dissolved in 80 ml of dichloromethane and the solution was stirred at 0° C. under nitrogen atmosphere. To this mixture was added 388 mg (3.17 mmol) of N,N'-dimethylaminopyridine, and the resulting mixture was stirred for 5 hours at 0° C. Water was added and the mixture was extracted with ether. The organic layer was washed with saturated saline and dried over anhydrous magnesium sulfate. The solvent was removed under reduced pressure and the resulting residue was purified by silica gel column chromatography to give 4.68 g (12.9 mmol) of the title compound 7.

The physicochemical data of the compound are as follows: FAB-MS, m/z: 364.2137 ((M+H)$^+$: $C_{20}H_{30}O_5N$, calculated value: 364.2124); $^1$H NMR (400 MHz, CDCl$_3$) δ ppm: 1.45 (9H, s), 1.2–2.3 (9H, m), 2.9–3.2 (2H, m), 3.3–3.8 (1H, m), 4.3–4.6 (1H, m), 4.9–5.0 (2H, m), 7.1–7.3 (5H, m); IR (cm$^{-1}$): 3437, 3362, 3028, 2938, 2864, 1712, 1503, 1452, 1366, 1169, 1057, 1014, 747, 700

Step 2: Synthesis of N-butoxycarbonyl-L-phenylalanine 2-oxocyclohexyl ester (compound 8)

To a solution of 3.1 g (8.53 mmol) of N-t-butoxycarbonyl-L-phenylalanine 2-hydroxycyclohexyl ester (compound 7) in 30 ml of acetone was added 30 ml of Jones reagent (1M solution) at 0° C., and the mixture was stirred for 30 minutes at the same temperature and for 3 hours at a room temperature. 2-Propanol was added to change the color of the solution to green, and the mixture was put in a separatory funnel and extracted with ether (three times). The organic layer was washed with saturated sodium carbonate aqueous solution and further with saturated saline, and dried over anhydrous magnesium sulfate. The solvent was removed under reduced pressure and the resulting residue was purified by silica gel column chromatography to give 2.70 g (7.47 mmol) of the title compound 8.

The physicochemical data of the compound are as follows: FAB-MS, m/z: 362.1971 ((M+H)$^+$: $C_{20}H_{28}O_5N$, calculated value: 362.1968); $^1$H NMR (400 MHz, CDCl$_3$) δ ppm: 1.39 (9H×0.5, s), 1.41 (9H×0.5, s), 1.63 (1H, m), 1.76 (2H, m), 1.97 (1H×0.5, m), 2.09 (1H×0.5, m), 2.22 (1H×0.5, m), 2.31 (1H×0.5, m), 2.41 (1H, dt, J=6.4, 13.7 Hz), 2.53 (1H, brd, J=13.7 Hz), 3.09 (1H×0.5, dd, J=7.3, 14.2 Hz), 3.12 (1H×0.5, dd, J=6.0, 13.5 Hz), 3.19 (1H×0.5, dd, J=5.9, 13.5 Hz), 3.33 (1H×0.5, dd, J=5.4, 14.2 Hz), 4.62 (1H×0.5, brq, J=6–7 Hz), 4.68 (1H×0.5, brq, J=6–7 Hz), 4.88 (1H×0.5, brd, J=8.8 Hz), 5.02 (1H×0.5, brd, J=7Hz), 5.14 (1H×0.5, brdd, J=6, 10 Hz), 5.22 (1H×0.5, dd, J=6.4, 11.2 Hz), 7.15–7.35 (5H, m); IR (cm–1): 3321, 2946, 2865, 1741, 1618, 1448, 1387, 1228, 1064, 1018, 758, 700

Step 3: Synthesis of (3S,4aS,8aS)-3-benzyl-4a-cyano-2-oxocyclo-hexa[e]tetrahydro-1,4-oxazine (compound 9)

To a solution of 3.1 g (8.59 mmol) of N-t-butoxycarbonyl-L-phenylalanine 2-oxocyclohexyl ester (compound 8) in 30 ml of dichloromethane was added 30 ml of trifluoroacetic acid at 0° C., and the mixture was stirred for 1 hour. The solvent was removed under reduced pressure and the resulting residue was dissolved in 150 ml of 2-propanol. To this solution was added 840 mng (17.2 mmol) of sodium cyanide and the mixture was stirred for 2 hours at a room temperature. After completion of the reaction, the solvent was removed under reduced pressure and the resulting residue was put in a separatory funnel with a small amount of ethyl acetate. Then, saturated sodium bicarbonate aqueous solution was added and the mixture was extracted with ether. The organic layer was washed with saturated saline and dried over anhydrous magnesium sulfate, then the solvent was removed under reduced pressure. $^1$H NMR analysis showed that the resulting residue contained the title compound 9 and its (3S,4aS,8aR)-enantiomer (compound 10) in the ratio 4:1. The residue was purified by silica gel short column chromatography and recrystallized from dichloromethane/ether to give 1.04 g (3.87 mmol) of compound 9 and 0.93 g (3.43 mmol) of the mixture of compounds 9 and 10.

The physicochemical data of compound 9 are as follows: mp. 153–55° C.; [α]$_D$–326.2° (c 0.52, CHCl$_3$); FAB-MS, m/z: 271.1437 ((M+H)$^+$: $C_{16}H_{19}O_2N_2$, calculated value: 271.1447); $^1$H NMR (400 MHz, CDCl$_3$) δ ppm: 1.29 (1H, tq, J=3.5, 12 Hz), 1.44–1.63 (4H, m), 1.73 (1H, ddt, J=2, 15, 4 Hz), 1.88–1.98 (2H, m), 2.01 (1H, ddt, J=2, 14, 4 Hz), 3.01 (1H, dd, J=9.0, 13.7 Hz), 3.42 (1H, dd, J=3.6, 13.7 Hz), 4.16 (1H, ddd, J=3.6, 4.9, 9.0 Hz), 4.38 (1H, ddd, J=2.0, 4.6, 10.7 Hz), 7.24–7.36 (5H, m); IR (cm$^{-1}$): 3300, 2932, 2862, 2820, 1729, 1443, 1381, 1182, 1058, 747, 701

Step 4: Synthesis of (4aS,8aS)-(Z)-3-benzylidenyl-4a-cyano-2oxocyclohexa[e]tetrahydro-1,4-oxazine (compound 11)

To a solution of 1.99 g (7.36 mmol) of (3S,4aS,8aS)-3-benzyl-4a-cyano-2-oxocyclohexa[e]tetrahydro-1,4-oxazine (compound 9) in 20 ml of dichloromethane and 95 ml of ether was added 2.08 ml (18.4 mmol) of t-butylhypochlorite at 0° C. under nitrogen gas atmosphere, and the mixture was stirred for 1 hour. Then, 3.08 ml (22.1 mmol) of triethylamine was added and the mixture was stirred for 2 hours at a room temperature. Ether was added to the reaction mixture and the resulting precipitate was removed by filtration. The solvent was removed under reduced pressure and the residue was purified by silica gel column chromatography to give 1.81 g (6.75 mmol) of the title compound 11.

The physicochemical data of the compound are as follows: mp. 186–188° C.; [α]$_D$–40.5° (c 0.46, CHCl$_3$); FAB-MS, m/z: 269.1277 ((M+H)$^+$: $C_{16}H_{17}O_2N_2$, calculated value: 269.1290) $^1$H NMR (400 MHz, CDCl$_3$) δ ppm: 1.50 (1H, m), 1.67 (1H, m), 1.74 (1H, m), 1.85 (1H, m), 1.9–2.0 (2H, m), 2.1–2.2 (2H, m), 4.6 (2H, m), 6.99 (1H, s), 7.3–7.4 (2H, m), 7.4–7.5 (3H, m); IR (cm$^{-1}$): 3204, 3039, 2856, 2665, 2547, 1704, 1608, 1487, 1449, 1381, 1222, 1194, 1142, 1060, 1029, 757, 695

Step 5: Synthesis of (4aS,8aR)-(Z)-3-benzylidenyl-4a-cyano-2-oxocyclohexa[e]tetrahydro-1,4-oxazine (compound 12)

To a solution of 1.99 g (7.36 mmol) of (3S,4aS, 8a(S and R))-3-benzyl-4a-cyano-2-oxocyclohexa[e]tetrahydro-1,4-oxazine (compound 9 and compound 10) in 20 ml of dichloromethane and 95 ml of ether was added 2.08 ml (18.4 mmol) of t-butylhypochlorite at 0° C. under nitrogen gas atmosphere, and the mixture was stirred for 1 hour. Then, 3.08 ml (22.1 mmol) of triethylamine was added and the mixture was stirred for 2 hours at a room temperature. After completion of the reaction, ether was added and the resulting precipitate was collected by filtration and purified by silica gel column chromatography with dichloromethane to give 950 mg (3.54 mmol) of the title compound 12. On the other hand, the filtrate was removed under reduced pressure and the resulting residue was purified by silica gel column chromatography to give 850 mg (3.17 mmol) of compound 11.

The physicochemical data of compound 12 are as follows: mp. 233–235° C.; [α]$_D$+166° (c 0.51, CHCl$_3$); FAB-MS, m/z: 269.1273 ((M+H)$^+$: $C_{16}H_{17}O_2N_2$, calculated value: 269.1290); $^1$H NMR (400 MHz, CDCl$_3$) δ ppm: 1.43 (1H, tq, J=4, 13 Hz), 1.71 (2H, m), 1.85 (2H, m), 1.97 (1H, m), 2.23 (2H, m), 4.30 (1H, dd, J=4.4, 11.7 Hz), 4.84 (1H, brs), 7.02 (1H, s), 7.31 (1H, dt, J=2.4, 6.4 Hz), 7.4 (4H, m); IR (cm$^{-1}$): 3302, 2959, 2863, 1712, 1607, 1457, 1382, 1253, 1201, 1058, 756, 693

Step 6: Synthesis of (1R,2S)-1-amino-2-hydroxycyclohexane-carboxylic acid (compound 1, n=2)

100 mg (0.37 mmol) of (4aS,8aS)-(Z)-3-benzylidenyl-4a-cyano- 2-oxocyclohexa[e]tetrahydro-1,4-oxazine (compound 11) was dissolved in 15 ml of dichloromethane, 30 ml of methanol and 10 ml of conc. HCl, and the mixture was stirred for 1 hour at 0° C., 12 hours at a room temperature, and further 3 hours at 100° C. The reaction mixture was concentrated to about 10 ml under reduced pressure, put in a separatory funnel, and washed with ether (twice). The water layer was concentrated under reduced pressure. The residue was dissolved in 10 ml of conc. HCl and heated at 100° C. in a sealed tube for 6 hours. After completion of the reaction, the reaction mixture was poured into water and washed with ether. The water layer was concentrated under reduced pressure, then the resulting residue was dissolved in water and purified by using Dowex 50W×4 ion exchange column chromatography (eluent: 1N ammonia solution) to give crude crystalline compound 1 (n=2). Recrystallization from methanol/ether gave 48 mg (0.30 mmol) of the title compound 1 (n=2).

The physicochemical data of the compound are as follows: mp. >270° C.; $[\alpha]_D$–33.1° (c 0.97, H$_2$O); FAB-MS, m/z: 160.0978 ((M+H)$^+$: C$_7$H$_{14}$O$_3$N, calculated value: 160.0974) $^1$H NMR (400 MHz, D$_2$O) δ ppm: 1.23–1.51 (3H, m), 1.72 (1H, brd-quint, J=14, 3 Hz), 1.83 (1H, m), 1.92–2.02 (3H, m), 4.19 (1H, dd, J=5.0, 11.5 Hz); IR (cm$^{-1}$): 3371, 3080, 3051, 2938, 2866, 1659, 1601, 1492, 1386, 1071, 778, 675

Step 7: Synthesis of (1R,2R)-1-amino-2-hydroxycyclohexanecarboxylic acid (compound 2, n=2)

100 mg (0.37 mmol) of (4aS,8aR)-(Z)-3-benzylidenyl-4a-cyano-2-oxocyclohexa[e]tetrahydro-1,4-oxazine (compound 12) was dissolved in 15 ml of dichloromethane, 30 ml of methanol and 10 ml of conc. HCl, and the mixture was stirred for 1 hour at 0° C., 12 hours at a room temperature, and further 3 hours at 100° C. The reaction mixture was concentrated to about 10 ml under reduced pressure, put in a separatory funnel, and washed with ether (twice). The water layer was concentrated under reduced pressure, and the residue was dissolved in 10 ml of conc. HCl and heated at 100° C. in a sealed tube for 6 hours. After completion of the reaction, the reaction mixture was poured into water and washed with ether. The water layer was concentrated under reduced pressure, then the resulting residue was dissolved in water and purified by using Dowex 50W×4 ion exchange column chromatography (eluent: 1N ammonia solution) to give crude crystalline compound 2 (n=2). Recrystallization from methanol/ether gave 37 mg (0.23 mmol) of the title compound 2 (n=2).

The physicochemical data of the compound are as follows: mp. >270° C.; $[\alpha]_D$–28.9° (c 0.15, H$_2$O); FAB-MS, m/z: 160.0975 ((M+H)$^+$: C$_7$H$_{14}$O$_3$N, calculated value: 160.0974); $^1$H NMR (400 MHz, D$_2$O) δ ppm: 1.22 (1H, tq, J=4, 12 Hz), 1.35–1.6 (3H, m), 1.63 (1H, brdt, J=12, 4 Hz), 1.70 (1H, dq, J=12, 4 Hz), 1.83 (1H, brdq, J=4, 12 Hz), 2.02 (1H, brdt, J=4, 12 Hz), 3.80 (1H, dd, J=4.4, 11.7 Hz); IR (cm$^{-1}$): 3547, 3348, 2902, 2857, 1592, 1515, 1418, 1394, 1353, 1277, 1096, 1049, 831, 787, 610

EXAMPLE 2

(1R,2S)-1-amino-2-hydroxycyclopentanecarboxylic acid (compound 1; n=1)

Step 1: Synthesis of N-t-butoxycarbonyl-L-phenylalanine 2,2-dimethoxycyclopentyl ester (compound 14)

A mixture of 1.39 g (5.24 mmol) of N-t-butoxycarbonyl-L-phenylalanine (compound 6), 714 mg (4.76 mmol) of 2-hydroxycyclopentanone dimethylacetal (compound 13) and 1.37 g (7.14 mmol) of 1-ethyl-3-(3-dimethylaminopropyl)carbodiimide. HCl (EDC) was dissolved in 30 ml of dichloromethane and stirred at 0° C. under nitrogen atmosphere. To this solution was added 63 mg (0.514 mmol) of N,N'-dimethylaminopyridine, and the resulting mixture was stirred for 5 hours at 0° C. Then, water was added and the mixture was extracted with ether. The organic layer was washed with saturated saline and dried over anhydrous magnesium sulfate. The solvent was removed under reduced pressure and the resulting residue was purified by silica gel column chromatography to give 1.68 g (4.28 mmol) of the title compound 14.

The physicochemical data of the compound are as follows: $^1$H NMR (300 MHz, CDCl$_3$) δ ppm: 1.18–2.13 (6H, m), 1.39 (9H×0.5, s), 1.42 (9H×0.5, s), 2.95–3.09 (2H, m), 3.16 (3H×0.5, s), 3.22 (3H, s), 3.23 (3H×0.5, s), 4.43 (1H×0.5, brs), 4.59 (1H, dt, J=6.9, 13.8 Hz), 4.89(1H×0.5, brs), 5.02 (1H×0.5, brd, J=5.3 Hz), 5.11 (1H×0.5, brd, J=5.5 Hz), 7.16–7.30 (5H, m); IR (cm$^{-1}$): 3473, 2984, 1722, 1618, 1498, 1456, 1370, 1252, 1170, 1052

Step 2: Synthesis of N-t-butoxycarbonyl-L-phenylalanine 2-oxocyclopentyl ester (compound 15)

To a solution of 450 mg (1.14 mmol) of N-t-butoxycarbonyl-L-phenylalanine 2,2-dimethoxycyclopentyl ester (compound 14) in 50 ml of acetone was added 32.5 mg (0.17 mmol) of p-toluenesulfonic acid at a room temperature and the mixture was stirred for 20 hours. Then, 25 ml of water and 28.7 mg (0.342 mmol) of sodium bicarbonate were added to the reaction mixture and acetone was removed under reduced pressure. The resulting residue was put in a separatory funnel with water and extracted with ether (three times). The organic layer was washed with saturated saline and dried over anhydrous magnesium sulfate. The solvent was removed under reduced pressure and the resulting residue was purified by silica gel column chromatography to give 390 mg (1.12 mmol) of the title compound 15.

The physicochemical data of the compound are as follows: $^1$H NMR (300 MHz, CDCl$_3$) δ ppm: 1.41 (9H, s), 1.73–2.45 (6H, m), 3.07–3.24 (2H, m), 4.47–5.18 (3H, m), 7.15–7.35 (5H, m); IR (cm$^{-1}$): 3460, 2498, 2256, 1748, 1710, 1608, 1496, 1454, 1370, 1166

Step 3: Synthesis of (3S,4aS,7aS)-3-benzyl-4a-cyano-2-oxocyclopenta[e]tetrahydro-1,4-oxazine (compound 16)

To a solution of 507 mg (1.46 mmol) of N-t-butoxycarbonyl-L-phenylalanine 2-oxocyclopentyl ester (compound 15) in 30 ml of dichloromethane was added 10 ml of trifluoroacetic acid at a room temperature and the mixture was stirred for 15 minutes. Then, toluene was added to the reaction mixture and the solvent was removed under reduced pressure. The resulting residue was dissolved in 30 ml of acetonitrile, and to this solution was added 599 mg (7.30 mmol) of sodium acetate and 878 mg (7.30 mmol) of anhydrous magnesium sulfate. The mixture was stirred for 1 hour. After completion of the reaction, toluene was added and the solvent was removed under reduced pressure. The resulting residue was dissolved in 30 ml of 2-propanol and to this solution was added 290 mg (2.92 mmol) of trimethylsilyl cyanide (TMSCN) and 1.46 ml (1.46 mmol) of zinc chloride (1.0 M solution). The mixture was stirred for 20 hours at a room temperature. After completion of the reaction, saturated sodium bicarbonate aqueous solution and water were added and the mixture was extracted with ether (twice). The organic layer was washed with water and saturated saline, and the solvent was removed. The resulting residue was recrystallized from ethyl acetate/hexane to give 325 mg (1.27 mmol) of the title compound 16.

The physicochemical data of the compound are as follows: mp. 111° C.; $[\alpha]_D$ −40.8° (c 1.0, CHCl$_3$); $^1$H NMR (300 MHz, CDCl$_3$) δ ppm: 1.69–2.30 (7H, m), 2.86 (1H, dd, J=9.8, 14.1 Hz), 3.52 (1H, dd, J=3.6, 14.1 Hz), 3.94 (1H, dt, J=3.6, 9.7 Hz), 4.78 (1H, t, J=6.3 Hz), 7.24–7.38 (5H, m); IR (cm$^{-1}$): 3340, 3036, 2964, 2256, 1754, 1496, 1442, 1384, 1220, 1176

Step 4: Synthesis of (4aS,7aS)-(Z)-3-benzylidenyl-4a-cyano-2-oxocyclopenta[e]tetrahydro-1,4-oxazine (compound 17)

To a solution of 1.89 g (7.36 mmol) of (3S,4aS,7aS)-3-benzyl-4a-cyano-2-oxocyclopenta[e]tetrahydro-1,4-oxazine (compound 16) in 95 ml of ether was added 2.08 ml (18.4 mmol) of t-butyl-hypochlorite at 0° C. under nitrogen gas atmosphere, and the mixture was stirred for 1 hour. Then 3.08 ml (22.1 mmol) of triethylamine was added and the mixture was stirred for 2 hours at a room temperature. After completion of the reaction, ether was added to the reaction mixture and the resulting precipitate was removed by filtration. The solvent was removed under reduced pressure and the residue was purified by silica gel column chromatography to give 1.46 g (5.74 mmol) of the title compound 17.

The physicochemical data of the compound are as follows: mp. 133–34° C.; $[\alpha]_D$+188° (c 0.50, CHCl$_3$); $^1$H NMR (300 MHz, CDCl$_3$) δ ppm: 1.84–2.46 (6H, m), 4.74 (1H, s), 4.94 (1H, dt, J=1.8, 7.4 Hz), 7.06 (1H, s), 7.30–7.47 (5H, m); IR (cm$^{-1}$): 3376, 2964, 2256, 1738, 1626, 1494, 1388, 1240, 1198, 1150

Step 5: Synthesis of (1R,2S)-1-amino-2-hydroxycyclopentanecarboxyllc acid (compound 1, n=1)

94 mg (0.37 mmol) of (4aS,7aS)-(Z)-3-benzylidenyl-4a-cyano-2-oxocyclopenta[e]tetrahydro-1,4-oxazine (compound 17) was dissolved in 10 ml of conc.HCl and was allowed to react in a sealed tube for 4 hours at 0° C. and further 24 hours at 80° C. The reaction mixture was put in a separatory funnel and washed with ether (twice). The water layer was concentrated under reduced pressure, and the resulting residue was dissolved in water and purified by using Dowex 50W×4 ion exchange column chromatography (eluent: 1N ammonia solution) to give crude crystalline compound 1 (n=1). Recrystallization from methanol/ether gave 42 mg (0.29 mmol) of the title compound 1 (n=1).

The physicochemical data of the compound are as follows:

mp. >250° C.; $[\alpha]_D$+20.5° (c 0.50, H$_2$O); $^1$H NMR (300 MHz, D$_2$O) δ ppm: 1.48–2.23 (6H, m), 4.37 (1H, t, J=7.5 Hz)

As mentioned above, the present invention provides optically active 1-amino-2-hydroxycycloalkanecarboxylic acid derivatives. They are novel compounds which, when introduced into a peptide or protein molecule, enable to fix the conformation of the molecule and inhibit hydrolysis with peptidases. Therefore, they are useful as reagents in peptide chemistry and protein engineering.

The derivatives of the present invention can be regarded as equivalent to naturally occurring amino acids such as serine and threonine. In view of the fact that serine and threonine have been known to act as the active centers of receptors and enzymes, and that the introduction of the derivatives of the present invention into a peptide or protein molecule enables to control the conformation of the molecule thereby giving stability against peptidases, studying the correlation between the structure and activity of compounds in which the derivatives of the present invention are introduced would lead to possibility to develop novel pharmaceutical preparations such as novel enzyme inhibitors.

What is claimed is:

1. A substantially pure (1R, 2S)-1-amino-2-hydroxycycloalkanecarboxylic acid represented by formula (1):

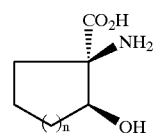

wherein n is 0, 1, 2, 3 or 4.

2. A substantially pure (1R, 2R)-1-amino-2-hydroxycycloalkanecarboxylic acid represented by formula (2):

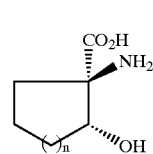

wherein n is 0, 1, 2, 3 or 4.

3. A substantially pure (1S, 2R)-1-amino-2-hydroxycycloalkanecarboxylic acid represented by formula (3):

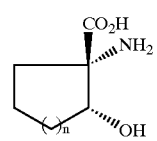

wherein n is 0, 3 or 4.

4. A substantially pure (1S, 2S)-1-amino-2-hydroxycycloalkanecarboxylic acid represented by formula (4):

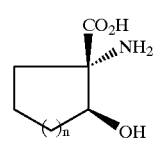

wherein n is 0, 3 or 4.

5. (1R, 2S)-1-amino-2-hydroxycyclohexanecarboxylic acid.

6. (1R, 2R)-1-amino-2-hydroxycyclohexanecarboxylic acid.

7. (1R, 2S)-1-amino-2-hydroxycyclopentanecarboxylic acid.

8. A method of synthesizing an (1R, 2R) or (1R, 2S) 1-amino-2-hydroxycycloalkanecarboxylic acid represented by the formula:

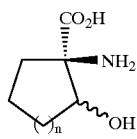

wherein n is 0, 1, 2, 3 or 4;
comprising the steps of:
(i) condensing a compound of the following formula:

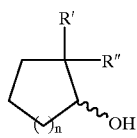

wherein n has the same definition as above; and
R' and R" independently are selected from the group consisting of H, OH and OR'", wherein R'" is a lower alkyl group;
with a N-protected-L-phenylalanine to produce a compound of the following formula:

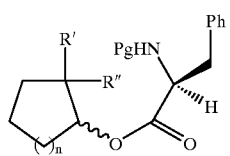

wherein n, R' and R" have the same definition as above; and
Pg is an amino protecting group;
(ii) oxidizing the product of step (i) to produce a compound wherein R' and R" taken together are a carbonyl group;
(iii) deprotecting the product of step (ii) by removing the amino protecting group;
(iv) cyclodehydrating the product of step (iii) with a cyanide equivalent;
(v) oxidizing the product of step (iv) to produce an enamine derivative having a formula selected from the group consisting of:

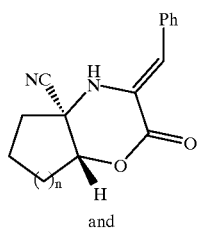

and

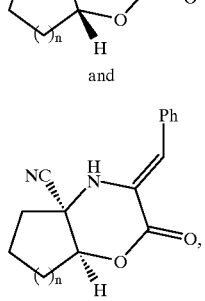

wherein n has the same definition as above; and (vi) treating the enamine derivative with an acid to produce the (1R, 2R) or (1R, 2S) 1-amino-2-hydroxycycloalkanecarboxylic acid.

9. The method of claim 8 wherein the N-protected-L-phenylalanine is N-tert-butoxycarbonyl-L-phenylalanine, and the amino protecting group is a tert-butylcarbonyl group.

10. The method of claim 8 wherein the cyanide equivalent is selected from the group consisting of sodium cyanide, potassium cyanide and trimethylsilyl cyanide.

11. The method of claim 8 further comprising the step of isolating after step (iv) or step (v) one stereoisomer of a pair of stereoisomers having the configuration (1R, 2R) or (1R, 2S), the pair of stereoisomers defining the product of step (iv) or (v).

12. The method of claim 8 wherein the (1R, 2R) 1-amino-2-hydroxycycloalkanecarboxylic acid is (1R, 2R) 1-amino-2-hydroxycyclohexanecarboxylic acid.

13. The method of claim 8 wherein the (1R, 2S) 1-amino-2-hydroxycycloalkanecarboxylic acid is (1R, 2S) 1-amino-2-hydroxycyclohexanecarboxylic acid.

14. The method of claim 8 wherein the (1R, 2S) 1-amino-2-hydroxycycloalkanecarboxylic acid is (1R, 2S) 1-amino-2-hydroxycyclopentanecarboxylic acid.

15. A method of synthesizing an (1S, 2R) or (1S, 2S) 1-amino-2-hydroxycycloalkanecarboxylic acid represented by the formula:

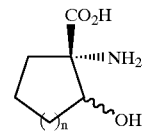

wherein n is 0, 1, 2, 3 or 4;
Comprising the steps of:
(i) condensing a compound of the following formula:

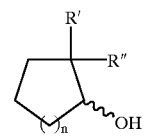

wherein n has the same definition as above; and
R' and R" independently are selected from the group consisting of H, OH and OR'", wherein R'" is a lower alkyl group;
with a N-protected-D-phenylalanine to produce a compound of the following formula:

wherein n, R' and R" have the same definition as above; and
Pg is an amino protecting group;
(ii) oxidizing the product of step (i) to produce a compound wherein R' and R" taken together are a carbonyl group;

(iii) deprotecting the product of step (ii) by removing the amino protecting group;
(iv) cyclodehydrating the product of step (iii) with a cyanide equivalent;
(v) oxidizing the product of step (iv) to produce an enamine derivative having a formula selected from the group consisting of:

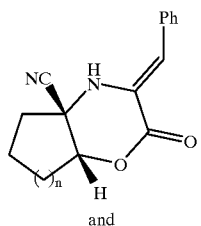
and

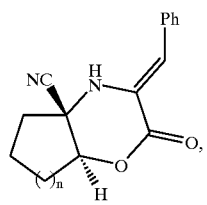

wherein n has the same definition as above; and
(vi) treating the enamine derivative with an acid to produce the (1S, 2R) or (1S, 2S) 1-amino-2-hydroxycycloalkanecarboxylic acid.

16. The method of claim 15 further comprising the step of isolating after step (iv) or step (v) one stereoisomer of a pair of stereoisomers having the configuration (1S, 2R) or (1S, 2S), the pair of stereoisomers defining the product of step (iv) or (v).

* * * * *

UNITED STATES PATENT AND TRADEMARK OFFICE
CERTIFICATE OF CORRECTION

PATENT NO.  : 5,959,141
DATED       : September 28, 1999
INVENTOR(S) : Horikawa et al.

Page 1 of 1

It is certified that error appears in the above-identified patent and that said Letters Patent is hereby corrected as shown below:

Claim 5,
Line 1, insert -- A substantially pure -- before "(1R, 2S)-1-amino-2-hydroxycyclohexanecarboxylic acid".

Claim 6,
Line 1, insert -- A substantially pure -- before "(1R,2R)-1-amino-2-hydroxycyclohexanecarboxylic acid".

Claim 7,
Line 1, insert -- A substantially pure -- before "(1R, 2S)-1-amino-2-hydroxycyclopentanecarboxylic acid".

Claim 9,
Line 3, delete "tert-butylcarbonyl" and replace it with -- tert-butoxycarbonyl --.

Signed and Sealed this

Third Day of July, 2001

Attest:

NICHOLAS P. GODICI
Attesting Officer
Acting Director of the United States Patent and Trademark Office